United States Patent [19]

Yasumoto et al.

[11] 4,092,313
[45] May 30, 1978

[54] PREPARATION OF 5-FLUOROPYRIMIDIN-4-ONE DERIVATIVES

[75] Inventors: Mitugi Yasumoto, Itano; Junichi Yamashita; Ichiro Yamawaki, both of Tokushima; Norio Unemi, Itano; Kenji Kitazato, Tokushima; Sadao Hashimoto, Itano; Setsuro Fujii, Tokushima, all of Japan

[73] Assignee: Taisho Pharmaceutical Company Limited, Tokyo, Japan

[21] Appl. No.: 729,980

[22] Filed: Oct. 6, 1976

Related U.S. Application Data

[62] Division of Ser. No. 1701,216, Jun. 30, 1976.

[30] Foreign Application Priority Data

Dec. 16, 1975  Japan .................... 50-150936
Dec. 16, 1975  Japan .................... 50-150937

[51] Int. Cl.$^2$ .......................................... C07D 239/36
[52] U.S. Cl. ................................................. 544/313
[58] Field of Search ................................ 260/251 R

[56] References Cited

U.S. PATENT DOCUMENTS 2,802,005  8/1957  Heidelberger et al. ......... 260/251 R
3,317,532  5/1967  Beaman et al. ..................... 260/251

OTHER PUBLICATIONS

Brown, The Pyrimidines, John Wiley & Sons, New York, 1962, pp. 201-203; 232.

*Primary Examiner*—Dolph H. Torrence
*Attorney, Agent, or Firm*—Toren, McGeady and Stanger

[57] ABSTRACT

A 5-fluoropyrimidin-4-one derivative represented by the formula

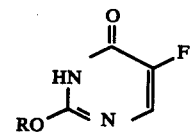

wherein R is straight-chain or branched-chain alkyl having 4 to 18 carbon atoms, straight-chain or branched-chain alkenyl having 2 to 18 carbon atoms, alkylene oxido having 3 to 10 carbon atoms, aryl or aralkyl;
    processes for preparing the derivative;
    an anti-tumor composition containing the derivative as an effective component and an excipient.

3 Claims, No Drawings

PREPARATION OF 5-FLUOROPYRIMIDIN-4-ONE DERIVATIVES

This is a division of application Ser. No. 701,216, filed June 30, 1976.

This invention relates to novel 5-fluoropyrimidin-4-one derivatives, to a process for preparing the same and to anti-tumor compositions containing the derivative as an effective component.

The 5-fluoropyrimidin-4-one derivatives of this invention are novel compounds represented by the formula

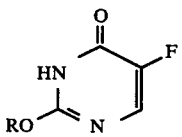 (1)

wherein R is straight-chain or branched-chain alkyl having 4 to 18 carbon atoms, straight-chain or branched-chain alkenyl having 2 to 18 carbon atoms, alkylene oxido having 3 to 10 carbon atoms, aryl or aralkyl.

Even since 5-fluorouracil was found to inhibit transplanted tumors by Heidelberger et al. as disclosed for example in Cancer Research, Vol. 18, page 305, 1958 the compound has been used as an anti-tumor agent for clinical purposes. Because of high toxicity, however, continued administration of 5-fluorouracil causes side effects such as loss of appetite, stomatitis, nausea, vomiting and like gastrointestinal disorders, leukopenia, thrombocytopenia and like disorders in the blood, disorders in the liver and kidney, etc.

To overcome the above drawback, we have conducted intensive research and found that the 5-fluoropyrimidin-4-one derivatives of this invention have very low toxicity and an outstanding anti-tumor effect. This invention has been accomplished based on this novel finding.

The 5-fluoropyrimidin-4-one derivatives of the formula (1) are obtained for example by reacting 2,4-dichloro-5-fluoropyrimidine of the formula

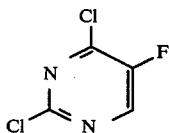 (2)

with an alcoholate or phenolate of the formula ROM wherein R is as defined above and M is alkali metal to prepare 2,4-disubstituted-5-fluoropyrimidine of the formula

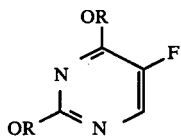 (3)

wherein R is as defined above, and hydrolyzing the fluoropyrimidine.

The compounds of this invention are prepared also by reacting 2-chloro-5-fluoropyrimidin-4-one of the formula

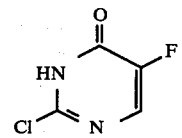 (4)

with an alcoholate or phenolate of the formula ROM wherein R and M are as defined above.

The 2,4-dichloro-5-fluoropyrimidine (2) used as a starting material of this invention is already known as disclosed for example in Collection of Czechoslovak Chemical Communications, Vol. 30, page 1900, 1965, etc.

The 2-chloro-5-fluoropyrimidin-4-one (4), another starting material of this invention, is also a known compound and is disclosed, for example, in Journal of Medicinal Chemistry, Vol. 8, page 253, 1965, etc.

The alcoholate or phenolate of the formula ROM used in this invention is also a known compound, in which the alkali metal represented by M is for example sodium or potassium. Such compound is readily obtainable by reacting an alcohol or phenol represented by ROH with an alkali metal compound such as metal sodium, metal potassium, sodium hydride, potassium hydride or the like. For this reaction, the alcohol or phenol, if solid, is preferably used as dissolved in absolute ethyl ether, dioxane, benzene or the like. Preferably the reaction is effected with heating when the reaction velocity is low. Examples of the groups represented by R of the formula ROM are straight-chain or branched-chain alkyl groups having 4 to 18 carbon atoms such as butyl, isobutyl, pentyl, hexyl, octyl, decyl, hexadecyl, octadecyl, etc.; straight-chain or branched-chain alkenyl group having 2 to 18 carbon atoms such as vinyl, allyl, butenyl, hexenyl, octenyl, 3,7-dimethyl-2,6-octadienyl, 9-octadecenyl, etc.; alkylene oxido groups having 3 to 10 carbon atoms and represented by

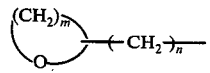

wherein m is an integer of 2 to 10, n is 0 or an integer of 1 to 8 and m + n = 3 to 10, such as 2,3-epoxypropyl, 9,10-epoxydecyl, tetrahydrofuryl, tetrahydrofurfuryl, tetrahydropyranyl, 1,5-epoxyhexyl, etc.; aryl groups such as phenyl, tolyl, xylyl, etc.; aralkyl groups such as benzyl, phenethyl, phenylpropyl, etc.

According to this invention, 2,4-dichloro-5-fluoropyrimidine (2) or 2-chloro-5-fluoropyrimidin-4-one (4) is reacted with a compound represented by ROM wherein R and M are as defined above. The reaction is effected preferably in an absolute nonprotonic solvent such as benzene, toluene, dioxane or the like. The alcohol or phenol used as a starting material for the preparation of ROM may be used as the solvent. The compound ROM is used preferably in an amount of about 2 to about 3 times the molar amount of the pyrimidine derivative (2) or (4). The reaction is conducted usually at about 50° to about 300° C.

2-Chloro-5-fluoropyrimidin-4-one (4), when used as the starting material, directly gives the desired compound (1) of this invention. Use of 2,4-dichloro-5-fluoropyrimidine (2) as the starting material first affords an intermediate, i.e. 2,4-disubstituted-5-fluoropyrimidine (3), which is subsequently hydrolyzed to give the desired compound (1). The intermediate (3) may be hydrolyzed after it has been isolated or without being isolated. The intermediate (3) is separated from the reaction mixture by a usual method such as extraction, distillation or recrystallization. When the intermediate is hydrolyzed as contained in the reaction mixture, it is preferable to distil off the solvent from the mixture prior to the hydrolysis. The hydrolysis reaction may be conducted by a usual method. For example, the intermediate or reaction mixture is suspended or dissolved in water or a solvent miscible with water such as methanol, ethanol, dioxane or the like. A basic substance such as a hydroxide or carbonate of alkali metal or alkaline earth metal is then added to the suspension or solution, and the mixture is usually heated to about 50° to about 150° C, whereby only the substituent at the 4-position of 2,4-disubstituted-5-fluoropyrimidine (3) is selectively hydrolyzed to give the 5-fluoropyrimidin-4-one derivative (1) of this invention. The progress of the reaction is ascertainable by thin-layer chromatography.

The compound of this invention obtained by either of the foregoing processes is readily separable for recovery by usual method. For example, the mixture resulting from the reaction is distilled to remove the solvent, dilute hydrochloric acid is added to the residue to adjust the pH to 4 to 6, and the mixture is extracted with methylene chloride, chloroform or the like. The extract is concentrated, and the concentrate is purified by a usual method such as recrystallization or column chromatography, whereby the compound of this invention is easily obtained.

The anti-tumor composition of this invention contains a pharmacologically effective amount of the present 5-fluoropyrimidin-4-one derivative and an excipient.

The anti-tumor composition of this invention can be formulated as various pharmaceutical preparations for varying routes of administration. For oral administration, tablets, capsules, soft capsules, granules, sustained release granules, fine particles, syrups are available. Non-oral preparations include parenteral solutions, suppositories, etc. For local administration, ointments are available. In view of the ease of formulation, storage stability and effectiveness, the composition may preferably be used in the form of capsules, soft capsules, granules, sustained release granules, fine particles and suppositories.

The excipients useful for making oral preparations such as tablets, capsules, granules, sustained release granules, fine particles, syrups, etc. are for example lactose, sucrose, starch, talc, magnesium stearate, crystalline cellulose, methyl cellulose, carboxymethyl cellulose, glycerin, sodium alginate, gum arabic, etc. Examples of coating materials for sustained release granules are Ethocel (trade mark, product of The Dow Chemical Co., U.S.A.), Eudragit (trade mark, product of Rohm & Haas Co., U.S.A.), etc. Examples of excipients for soft capsules are edible oils and fats having a melting point of up to 40° C such as sesame oil, rapeseed oil, medium chain triglyceride oil, etc. When desired, a surfactant, suspending agent, silicon dioxide and the like may be used for the preparation of capsules.

The amount of the effective component in oral preparations may preferably be 200 to 500 mg per dosage unit. Suitable carriers for preparing suppositories are for example cacao butter, Witepsol-W35 (fat, trade mark, product of Dynamit Nobel A.G. of Germany). The suppositories may preferably contain 500 to 1,000 mg of the effective component per piece. The dose per day of such oral preparations, suppositories, etc. for systemic administration may suitably be 800 to 1,500 mg calculated as the effective component.

Examples of suitable carriers for ointments for local administration are liquid paraffin, cetyl alcohol, white vaseline, squalane, hydrous lanolin, cholesterol, stearyl alcohol and like oily or fatty materials. Preferably the amount of effective component of ointments is 5 to 10 wt. %.

Given below are examples of the preparation of 5-fluoropyrimidin-4-one derivatives, examples of the preparation of anti-tumor compositions containing the derivative as an effective component, and the results obtained by testing the anti-tumor compositions for acute toxicity and pharmacological activity.

EXAMPLE 1

A 9.8 g quantity of metal potassium is dissolved in 300 ml of absolute n-butanol, 16.7 g of 2,4-dichloro-5-fluoropyrimidine is added to the solution and the mixture is stirred at 60° to 70° C for 5 hours. After the reaction, the solvent is distilled off, 50 ml of water is added to the residue and the mixture is extracted with 300 ml of toluene. The toluene layer is washed with water, dried and concentrated. The concentrate is distilled at reduced pressure to give 20.6 g of colorless oily 2,4-di(n-butoxy)-5-fluoropyrimidine in a yield of 85.1%, b.p. 125°–126° C/3–4 mm Hg.

|  | Elementary analysis (for $C_{12}H_{19}N_2O_2F$) | | |
|---|---|---|---|
|  | C | H | N |
| Calcd. (%): | 59.49 | 7.90 | 11.56 |
| Found (%): | 59.69 | 8.19 | 11.27 |

EXAMPLE 2

A 5.8 g quantity of metal sodium is dissolved in 300 ml of absolute n-butanol, 16.7 g of 2,4-dichloro-5-fluoropyrimidine is added to the solution and the mixture is refluxed for 3 hours. After the reaction, the solvent is distilled off, 350 ml of 2N aqueous potassium hydroxide solution is added to the residue and the mixture is refluxed for 10 hours with stirring. The resulting reaction mixture is cooled and extracted with 100 ml of ether twice to remove ether-soluble substances. Dilute hydrochloric acid is added to the aqueous layer to adjust the pH to 4–5 and to separate out crystals. The product is recrytallized from ethanol to give 15.5 g of white crystalline 2-n-butoxy-5-fluoropyrimidin-4-one in a yield of 83.3%, m.p. 127°–129.5° C.

|  | Elementary analysis (for $C_8H_{11}N_2O_2F$) | | |
|---|---|---|---|
|  | C | H | N |
| Calcd.(%): | 51.61 | 5.95 | 15.05 |
| Found (%): | 51.43 | 5.78 | 14.97 |

EXAMPLE 3

A 36.3 g quantity of n-hexadecanol is dissolved in 200 ml of absolute ether, 3.3 g of metal sodium is added to the solution and the mixture is refluxed until the sodium has been completely dissolved. Subsequently 8.5 g of 2,4-dichloro-5-fluoropyrimidine is added to the solution, and the mixture is refluxed for 3 hours. The resulting reaction mixture is washed with a small amount of water, and the ethereal layer is concentrated to separate out crystals, which are recrystallized from ethanol to give 18.6 g of white crystalline 2,4-di(n-hexadecyloxy)-5-fluoropyrimidine in a yield of 63.1%, m.p. 62°–63° C.

| Elementary analysis (for $C_{36}H_{67}N_2O_2F$) | | | |
|---|---|---|---|
| | C | H | N |
| Calcd. (%): | 74.69 | 11.67 | 4.84 |
| Found (%): | 74.55 | 11.72 | 4.77 |

A 2.9 g portion of the 2,4-di-(n-hexadecyloxy)-5-fluoropyrimidine is dissolved in a mixture of 5 ml of 2N aqueous potassium hydroxide solution and 25 ml of ethanol, and the solution is refluxed for 4 hours. The ethanol is distilled off from the resulting reaction mixture, and 50 ml of ether is added to the residue to remove ether-soluble substances. Dilute hydrochloric acid is added to the remaining mass to adjust the pH to 4–5 and to separate out crystals, which are recrystallized from ethanol to give 1.3 g of white crystalline 2-n-hexadecyloxy-5-fluoropyrimidin-4-one in a yield of 73.0%, m.p. 97°–98° C.

| Elementary analysis (for $C_{20}H_{35}N_2O_2F$) | | | |
|---|---|---|---|
| | C | H | N |
| Calcd. (%): | 67.76 | 9.95 | 7.20 |
| Found (%): | 67.59 | 10.21 | 7.45 |

EXAMPLE 4

A 5.8 g quantity of metal sodium is dissolved in a mixture of 100 ml of benzyl alcohol and 200 ml of toluene, 16.7 g of 2,4-dichloro-5-fluoropyrimidine is added to the solution, and the mixture is refluxed for 4 hours. The resulting reaction mixture is washed with water, dried and distilled at reduced pressure to give 27.0 g of colorless oily 2,4-di(benzyloxy)-5-fluoropyrimidine in a yield of 87.1%, b.p. 205°–206° C/3–4 mm Hg and m.p. 48.5°–49.5° C.

| Elementary analysis (for $C_{18}H_{15}N_2O_2F$) | | | |
|---|---|---|---|
| | C | H | N |
| Calcd. (%): | 69.67 | 4.87 | 9.03 |
| Found (%): | 69.94 | 5.06 | 8.75 |

EXAMPLE 5

A 6.9 g quantity of metal sodium is added to a mixture of 28 g of phenol and 200 ml of toluene, and the resulting solution is refluxed for 1 hour with stirring. Subsequently 16.7 g of 2,4-dichloro-5-fluoropyrimidine is added to the solution, and the mixture is refluxed for 4 hours. The resulting reaction mixture is thereafter treated in the same manner as in Example 2 to give 17.3 g of white crystalline 2-phenoxy-5-fluoropyrimidin-4-one in a yield of 84.0%, m.p. 224°–224.5° C.

| Elementary analysis (for $C_{10}H_7N_2O_2F$) | | | |
|---|---|---|---|
| | C | H | N |
| Calcd. (%): | 58.26 | 3.42 | 13.59 |
| Found (%): | 57.98 | 3.34 | 13.54 |

EXAMPLE 6

A 5.8 g quantity of metal sodium is dissolved in 300 ml of absolute n-butanol, 14.9 g of 2-chloro-5-fluoropyrimidin-4-one is added to the solution and the mixture is heated in a sealed tube at 140° to 150° C for 5 hours for reaction. The solvent is distilled off from the reaction mixture, 50 ml of water is added to the residue and the pH of the mixture is adjusted to 4–5 to separate out crystals, which are recrystallized from ethanol to give 17.1 g of white crystalline 2-n-butoxy-5-fluoropyrimidin-4-one in a yield of 91.9%, m.p. 127°–129° C.

| Elementary analysis (for $C_8H_{11}N_2O_2F$) | | | |
|---|---|---|---|
| | C | H | N |
| Calcd. (%): | 51.61 | 5.95 | 15.05 |
| Found (%): | 51.40 | 5.80 | 15.00 |

EXAMPLE 7

A 300 ml quantity of absolute sec-butanol, 5.8 g of metal sodium and 14.9 g of 2-chloro-5-fluoropyrimidin-4-one are treated in the same manner as in Example 6 to obtain crystals, which are then recrystallized from a water-ethanol mixture to give 17.0 g of white crystalline 2-sec-butoxy-5-fluoropyrimidin-4-one in a yield of 91.4%, m.p. 104°–105° C.

| Elementary analysis (for $C_8H_{11}N_2O_2F$) | | | |
|---|---|---|---|
| | C | H | N |
| Calcd. (%): | 51.61 | 5.95 | 15.05 |
| Found (%): | 51.43 | 5.80 | 15.21 |

EXAMPLES 8 to 11

The same procedure as in Example 6 is repeated except the n-pentanol, n-hexanol, n-decanol and n-hexadecanol are used as the alcohol to obtain corresponding desired compounds. The properties and yields of the compounds are given below.

2-n-Pentyloxy-5-fluoropyrimidin-4-one

M.p. 117°–118° C, yield 90.3%.

| Elementary analysis (for $C_9H_{13}N_2O_2F$) | | | |
|---|---|---|---|
| | C | H | N |
| Calcd. (%): | 6.55 | 53.99 | 13.99 |
| Found (%): | 6.63 | 53.91 | 13.79 |

2-n-Hexyloxy-5-fluoropyrimidin-4-one

M.p. 114°–115° C, yield 86.1%.

| Elementary analysis (for $C_{10}H_{15}N_2O_2F$) | | | |
|---|---|---|---|
| | C | H | N |
| Calcd. (%): | 56.06 | 7.06 | 13.08 |
| Found (%): | 55.44 | 7.36 | 12.94 |

2-n-Decyloxy-5-fluoropyrimidin-4-one

M.p. 100°–101° C, yield 84.3%.

| Elementary analysis (for $C_{14}H_{23}N_2O_2F$) | | | |
|---|---|---|---|
| | C | H | N |
| Calcd. (%): | 57.29 | 7.90 | 9.54 |
| Found (%): | 57.45 | 7.92 | 9.30 |

2-n-Hexadecyloxy-5-fluoropyrimidin-4-one

M.p. 97°–98° C, yield 84.1%.

| Elementary analysis (for $C_{20}H_{35}N_2O_2F$) | | | |
|---|---|---|---|
| | C | H | N |
| Calcd. (%): | 67.76 | 9.95 | 7.20 |
| Found (%): | 67.50 | 10.03 | 7.41 |

EXAMPLE 12

23.1 g of 3,7-dimethyl-2,6-octadien-1-ol and 3.4 g of metal sodium are added to 200 ml of absolute toluene, and the mixture is stirred at 40° to 50° C until the metal sodium has been completely dissolved. Subsequently 7.4 g of 2-chloro-5-fluoropyrimidin-4-one is added to the solution, and the mixture is refluxed for 8 hours. The solvent is distilled off from the resulting reaction mixture, 30 ml of water is added to the residue and the pH of the mixture is adjusted to 4–5 with dilute hydrochloric acid. The resulting mixture is extracted with 200 ml of chloroform and the extract is concentrated. Purification of the residue by silica gel column chromatography gives 8.3 g of slightly yellow oily 2-(3,7-dimethyl-2,6-octadien-1-oxy)-5-fluoropyrimidin-4-one in a yield of 61.0%.

| Elementary analysis (for $C_{14}H_{19}N_2O_2F \cdot \frac{1}{2}H_2O$) | | | |
|---|---|---|---|
| | C | H | N |
| Calcd. (%): | 62.09 | 7.26 | 10.34 |
| Found (%): | 62.01 | 7.05 | 10.21 |

EXAMPLE 13

A 100 ml quantity of benzyl alcohol and 7.2 g of sodium hydride are added to 100 ml of absolute toluene, and the mixture is refluxed for 1 hour. Subsequently 14.9 g of 2-chloro-5-fluoropyrimidin-4-one is added to the reaction mixture, and the resulting mixture is heated in a sealed tube at 140° to 150° C for 6 hours for reaction. The reaction mixture is further treated in the same manner as in Example 6 to give 17.2 g of white crystalline 2-benzyloxy-5-fluoropyrimidin-4-one in a yield of 78.2%, m.p. 146°–147° C.

| Elementary analysis (for $C_{11}H_9N_2O_2F$) | | | |
|---|---|---|---|
| | C | H | N |
| Calcd. (%): | 60.00 | 4.12 | 12.72 |
| Found (%) | 60.21 | 4.08 | 12.55 |

EXAMPLE 14

A 11.7 g quantity of metal potassium is added to 200 ml of absolute toluene, and a mixture of 28 g of phenol and 100 ml of absolute toluene is further added dropwise to dissolve the potassium. Subsequently 14.9 g of 2-chloro-5-fluoropyrimidin-4-one is added to the solution, and the mixture is stirred at 100° C for 8 hours. The reaction mixture is thereafter treated in the same manner as in Example 6 to give 13.2 g of white crystalline 2-phenoxy-5-fluoropyrimidin-4-one in a yield of 64.1%, m.p. 224°–225° C.

| Elementary analysis (for $C_{10}H_7N_2O_2F$) | | | |
|---|---|---|---|
| | C | H | N |
| Calcd. (%): | 58.26 | 3.42 | 13.59 |
| Found (%) | 58.01 | 3.40 | 13.41 |

EXAMPLE 15

A 40 g quantity of tetrahydrofurfuryl alcohol and 7.2 g of sodium hydride are added to 200 ml of absolute toluene, and the mixture is stirred at 75°–80° C for 15 hours. Subsequently 14.9 g of 2-chloro-5-fluoropyrimidin-4-one is added to the reaction mixture, and the resulting mixture is heated in a sealed tube at 148° to 150° C for 5 hours for reaction. The resulting reaction mixture is treated in the same manner as in Example 6 to give 15.4 g of white crystalline 2-tetrahydrofurfuryloxy-5-fluoropyrimidin-4-one in a yield of 72.0%, m.p. 89°–91° C.

| Elementary analysis (for $C_9H_{11}N_2O_3F$) | | | |
|---|---|---|---|
| | C | H | N |
| Calcd. (%): | 50.47 | 5.18 | 13.08 |
| Found (%): | 50.19 | 5.11 | 13.22 |

Examples of the preparation of anti-tumor compositions of this invention will be given below.

PREPARATION EXAMPLE 1

A 6 g quantity of magnesium stearate and 44 g of lactose are thoroughly stirred to prepare a uniform mixture, to which 50 g of lactose and 100 g of crystalline cellulose are further added, and the mass is stirred. Finely divided 2-n-butoxy-5-fluoropyrimidin-4-one (200 g) is then admixed with the resulting mixture to obtain a powdery preparation. The preparation is encapsulated to produce capsules each containing 400 mg of the powdery preparation.

PREPARATION EXAMPLE 2

A 3 g quantity of magnesium stearate, 10 g of carboxymethyl cellulose calcium and 44 g of crystalline cellulose are stirred to obtain a uniform mixture, to which 250 g of finely divided 2-benzyloxy-5-fluoropyrimidin-4-one is then admixed. The mixture is made into slugs by a slugging machine, then granulated by an oscillator equipped with a No. 10 screen, and the granules are separated by a No. 30 screen, the screens being those specified by the Japanese Pharmacopoeia. A 3 g quantity of magnesium stearate is added to the granules remaining on the screen, and the mixture is made into crude tablets, each of the tablets weighing 310 mg. The tablets can be sugar- or film-coated.

PREPARATION EXAMPLE 3

A 4 kg quantity of finely divided 2-n-butoxy-5-fluoropyrimidin-4-one, 3 kg of corn starch, 1.5 kg of lactose and 1.4 kg of white sugar are placed into a flow coater and mixed together for 15 minutes. A solution of 200 g of carboxymethyl cellulose in 15 liters of 30% methanol is applied by spray coating to the flowing powder in an amount of 10 g calculated as carboxymethyl cellulose sodium per 990 g of the powder. The resulting mass is dried and screened to obtain fine particles containing 400 mg of 2-n-butoxy-5-fluoropyrimidin-4-one per gram of the particles.

PREPARATION EXAMPLE 4

A 2 kg quantity of finely divided 2-n-butoxy-5-fluoropyrimidin-4-one is uniformly mixed with 3 kg of medium chain fatty acid triglyceride, and the mixture is enclosed into soft capsules each containing 200 mg of 2-n-butoxy-5-fluoropyrimidin-4-one.

PREPARATION EXAMPLE 5

A 2.5 kg of lactose, 1.45 kg of starch and 5 kg of 2-benzyloxy-5-fluoropyrimidin-4-one are mixed together, 500 ml of 10% alcohol solution of hydroxypropyl cellulose is added to the mixture and the wet mixture is granulated. The granules are dried and screened. The granules are placed into a flow coater, and a 10% solution of Ethocel (trade mark, product of The Dow Chemical Co., U.S.A.) in a mixture of methylene chloride and n-hexane (1:1 in weight ratio) is sprayed onto the granules in an amount of 100 g calculated as Ethocel per 900 g of the granules to obtain sustained release granules. When subjected to dissolving test, the granular preparation is found to release 2-benzyloxy-5-fluoropyrimidin-4-one over a period of 18 hours.

PREPARATION EXAMPLE 6

A 1,400 g quantity of Witepsol-W35 (trade mark, as defined before) is melted by heating to 60° C, and 750 g of finely divided 2-benzyloxy-5-fluoropyrimidin-4-one is added in small portions to the molten mass to obtain a uniform mixture by stirring. The mixture is then cooled to 40° C and thereafter placed into 10 plastic containers each in a specified amount. The containers are passed through a cooling tank at 15° to 20° C to solidify the contents. The opening of each container is sealed to prepare suppositories.

PREPARATION EXAMPLE 7

A 100 g quantity of liquid paraffin, 50 g of cetyl alcohol and 797 g of vaseline are melted at an elevated temperature of 80° C, and 3 g of cholesterol and 50 g of finely divided 2-benzyloxy-5-fluoropyrimidin-4-one are then added to the molten mixture with thorough stirring. The resulting mixture is allowed to stand at room temperature and, when solidified to suitable hardness, the mixture is filled into a container to prepare an ointment.

Compounds of this invention are tested for acute toxicity and anti-tumor effect by the following methods.

Acute Toxicity

The compound of this invention is orally administered to mice, and the mice are checked 3 days, one week, 2 weeks and 3 weeks later for motality in terms of $LD_{50}$ calculated according to the method of Litchfield and Wilcoxon. The results are given in Table 1 below, which also shows the results obtained in the same manner as above with use of 5-fluorouracil for comparison.

Table 1

| Compound | (in mg/kg) Period | | | |
|---|---|---|---|---|
| | 3 Days | 1 Week | 2 Weeks | 3 Weeks |
| 2-n-Butoxy-5-fluoro-pyrimidin-4-one | 945 | 945 | 945 | 945 |
| 2-Benzyloxy-5-fluoro-pyrimidin-4-one 5-Fluorouracil | 894 | 894 | 894 | 894 |

Table 1-continued

| Compound | (in mg/kg) Period | | | |
|---|---|---|---|---|
| | 3 Days | 1 Week | 2 Weeks | 3 Weeks |
| (for comparison) | — | 200 | 145 | 115 |

Anti-tumor Effect

Cells of Ehrlich carcinoma or sarcoma 180, 5 × 10⁶ in number, are subcutaneously transplanted in a mouse. Twenty-four hours after the transplantation and during a subsequent period, the compound of this invention is orally given to the test animal once every day for 7 consecutive days. On the 10th day from the transplantation, the weight of tumor in the test animal is measured to determine the percentage of inhibition achieved by the compound relative to the weight of tumor in the control group. The results are given in Table 2 below, which also shows the results obtained in the same manner as above with use of 5-fluorouracil for comparison.

Table 2

| Compound | Dose (mg/kg/day) | Inhibition percentage (%) | |
|---|---|---|---|
| | | Ehrlich carcinoma | sarcoma 180 |
| 2-n-Butoxy-5-fluoro-pyrimidin-4-one | 90 | 64 | 62 |
| 2-Benzyloxy-5-fluoro-pyrimidin-4-one | 90 | 52 | 70 |
| 5-Fluorouracil (for comparison) | 30 | 61 | 64 |

What is claimed is:

1. A process of preparing a 5-fluoropyrimidin-4-one derivative of the formula wherein
R is straight-chain or branched-chain alkyl having 4 to 18 carbon atoms, straight-chain or branched-chain alkenyl having 2 to 18 carbon atoms, alkylene oxido having 3 to 10 carbon atoms, aryl or aralkyl, comprising reacting 2,4-dichloro-5-fluoropyrimidine with an alcoholate or phenolate of the formula ROM wherein R is as defined above and M is an alkali metal to obtain a 2,4-di-substituted-5-fluoropyrimidine derivative of the formula wherein
R is as defined above, and hydrolyzing the derivative in the presence of a basic substance.
2. The process of claim 1 wherein the basic substance is a hydroxide or carbonate of an alkali or alkaline earth metal.
3. A process for preparing a 5-fluoropyrimidin-4-one derivative of the formula

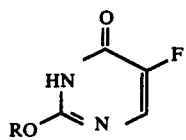
wherein
R is straight-chain or branched-chain alkyl having 4 to 18 carbon atoms, straight-chain or branched-chain alkenyl having 2 to 18 carbon atoms, alkylene oxido having 3 to 10 carbon atoms, aryl or aralkyl, comprising reacting 2-chloro-5-fluoropyrimidin-4-one with an alcoholate or phenolate of the formula ROM wherein R is as defined above and M is an alkali metal.
* * * * *

UNITED STATES PATENT OFFICE
CERTIFICATE OF CORRECTION

Patent No. 4,092,313     Dated May 30, 1978

Inventor(s) Mitugi Yasumoto, J. Yamashita, et al

It is certified that error appears in the above-identified patent and that said Letters Patent are hereby corrected as shown below:

In the heading of the Patent [73] should read as follows:

[73]    Assignee:    Taiho Pharmaceutical Company Limited
Tokyo, JAPAN

Signed and Sealed this

Sixth Day of February 1979

[SEAL]

Attest:

RUTH C. MASON
*Attesting Officer*

DONALD W. BANNER
*Commissioner of Patents and Trademarks*